US011727516B2

(12) United States Patent
Solakhyan et al.

(10) Patent No.: US 11,727,516 B2
(45) Date of Patent: Aug. 15, 2023

(54) SYSTEM AND METHODS FOR SECURING A DRUG THERAPY

(71) Applicant: PharmaCCX, Inc., Boston, MA (US)

(72) Inventors: Armen Solakhyan, Boston, MA (US); Peter Rice, Boston, MA (US); Richard Bergström, Boston, MA (US); Patrick Schneider, Boston, MA (US); Cole Boskey, Boston, MA (US)

(73) Assignee: PHARMACCX, INC., Boston, MA (US)

( * ) Notice: Subject to any disclaimer, the term of this patent is extended or adjusted under 35 U.S.C. 154(b) by 0 days.

(21) Appl. No.: 16/914,008

(22) Filed: Jun. 26, 2020

(65) Prior Publication Data

US 2020/0410618 A1 Dec. 31, 2020

Related U.S. Application Data

(60) Provisional application No. 62/947,453, filed on Dec. 12, 2019, provisional application No. 62/867,014, filed on Jun. 26, 2019.

(51) Int. Cl.
*G06Q 50/18* (2012.01)
*G16H 20/10* (2018.01)
(Continued)

(52) U.S. Cl.
CPC ......... *G06Q 50/188* (2013.01); *G06F 16/258* (2019.01); *G06Q 30/0206* (2013.01);
(Continued)

(58) Field of Classification Search
CPC ............. G06Q 50/188; G06Q 30/0206; G06Q 30/0234; G16H 20/10; G16H 70/40;
(Continued)

(56) References Cited

U.S. PATENT DOCUMENTS

2007/0162303 A1\* 7/2007 Wiley, II ............... G16H 20/10
705/2
2011/0054935 A1 3/2011 Hardaway
(Continued)

FOREIGN PATENT DOCUMENTS

MX PA04008737 7/2005
WO WO-2014/151911 9/2014

OTHER PUBLICATIONS

Notification of International Search Report and Written Opinion dated Sep. 8, 2020 received in related PCT Application No. PCT/US20/39876 (9 pages).

(Continued)

*Primary Examiner* — Robert A Sorey
*Assistant Examiner* — Kimberly A. Sass
(74) *Attorney, Agent, or Firm* — Wilmer Cutler Pickering Hale and Dorr LLP

(57) ABSTRACT

A system for customizing user parameters relating to a pharmaceutical treatment, receives, a first set of parameters associated with the pharmaceutical treatment, that indicate factors associated with the pharmaceutical treatment, in a first format. The system determines a subset of the set of first parameters based on the one or more factors and converts them into a second format. The system provides the second set of parameters to a second computing device, receives from the second computing device, a third set of parameters, wherein the third set of parameters are based on the one or more factors, the third set of parameters being provided in a third format, converts the third set of parameters from the second third format to the first format based on a second set of parameters, and present the converted third set of parameters received from the second computing device to the first computing device party.

20 Claims, 11 Drawing Sheets

(51) Int. Cl.
*G16H 70/40* (2018.01)
*G16H 50/20* (2018.01)
*G16H 50/70* (2018.01)
*G16H 50/30* (2018.01)
*G16H 70/20* (2018.01)
*G06Q 30/0201* (2023.01)
*G06F 16/25* (2019.01)
*G06Q 30/0234* (2023.01)
*A61B 5/107* (2006.01)

(52) U.S. Cl.
CPC ......... *G06Q 30/0234* (2013.01); *G16H 20/10* (2018.01); *G16H 50/20* (2018.01); *G16H 50/30* (2018.01); *G16H 50/70* (2018.01); *G16H 70/20* (2018.01); *G16H 70/40* (2018.01); *A61B 5/1072* (2013.01)

(58) Field of Classification Search
CPC ........ G16H 50/20; G16H 50/70; G16H 50/30; G16H 70/20; G06F 16/258; A61B 5/1072
See application file for complete search history.

(56) References Cited

U.S. PATENT DOCUMENTS

| | | | |
|---|---|---|---|
| 2011/0106554 A1* | 5/2011 | Benja-Athon | G06Q 40/08 705/2 |
| 2013/0211847 A1* | 8/2013 | Vaidya | G16H 10/60 705/2 |
| 2015/0324543 A1* | 11/2015 | List | G16H 50/20 705/2 |
| 2017/0061102 A1* | 3/2017 | Weber | G06F 19/00 |
| 2018/0330060 A1 | 11/2018 | Biles et al. | |

OTHER PUBLICATIONS

European Extended Search Report issued in European Application No. 20831045.8, dated May 3, 2023 (9 pages).

* cited by examiner

FIG. 8

SYSTEM AND METHODS FOR SECURING A DRUG THERAPY

CROSS REFERENCE TO RELATED APPLICATIONS

This application claims the benefit of U.S. provisional application 62/867,014, entitled "SYSTEM AND METHODS FOR IMPLEMENTING AN EXCHANGE TO EXPEDITE NEGOTIATIONS," filed Jun. 26, 2019, and U.S. provisional application 62/947,453 entitled "SYSTEMS AND METHODS FOR IMPLEMENTING AN EXCHANGE TO EXPEDITE NEGOTIATIONS," filed on Dec. 12, 2019, the contents of which are incorporated herein in their entirety.

TECHNICAL FIELD

The present disclosure relates to a platform that accelerates complex decision-making processes that may span organizations and incorporate elements of problem-solving, negotiation, and cooperation.

BACKGROUND

Entirely new types of drug therapies are being developed by public research organizations and private sector innovators to combat various illnesses. Scientific breakthroughs in genomics, epigenetics, and system biology are paying off. Drug pipelines are full of breakthroughs including targeted immunotherapy, cell and gene therapy, and others.

However, today's market access processes lag scientific innovation. Pharmaceutical companies and governments are excited for innovative pricing strategies, like indication and value-based pricing, for new innovative drugs, but negotiations between the parties take too long, even with just two parties involved. With three or more parties, the negotiations are even more complicated, and often not allowed due to anti-trust concerns. As a result, there is a logjam of various drug therapies that have been approved by regulators, but not yet reaching the patients. Patients are not getting the medicines that they need; companies are not selling their newest therapies; and governments and providers are not able to serve their patients. A new negotiation system is needed that reflects the scientific innovations and the new reality of therapies on the market.

SUMMARY

In some embodiments, a computerized system for customizing user parameters relating to securing a pharmaceutical treatment, comprising a memory, and a processor communicatively coupled to memory, wherein the processor is configured to receive from a first computing device, a first set of parameters associated with the pharmaceutical treatment, wherein one or more of the first set of parameters are indicative of one or more factors associated with the pharmaceutical treatment, the one or more first set of parameters being provided in a first format, based on the information received in the first set of parameters, transform the received first set of parameters to a second set of parameters, wherein transforming the first set of parameters to the second set of parameters includes determining a subset of the set of first parameters based on the one or more factors, determining a second format for the first parameters based on the one or more factors. The computerized system provides the second set of parameters to a second computing device, receives from the second computing device, a third set of parameters associated with the pharmaceutical treatment, wherein the third set of parameters are based on the one or more factors associated with the treatment, the third set of parameters being provided in a third format, converts the second third set of parameters negotiating price from the second third format to the first format based on a second set of parameters, and presents the converted third set of parameters received from the second computing device to the first computing device party.

In some embodiments, the first set of parameters include a number of patients eligible for the pharmaceutical treatment, duration of the treatment, expected price of the pharmaceutical treatment per patient, and expected rebate per patient. In some embodiments, the number of patients eligible for the pharmaceutical treatment may be one. In some embodiments, the computerized system configured to determine a subset of the first set of parameters, is further configured to exclude one or more parameters of the first set of parameters based on determining that the one or more parameters associated with the first set of parameters has a hide flag associated with it. In some embodiments, the one or more factors associated with the pharmaceutical treatment include a predetermined average patient height, a predetermined average patient weight, and a predetermined average patient surface area, and a duration of treatment.

In some embodiments, the computerized system of claim is further configured to determine an average dose requirement of the pharmaceutical treatment per patient based on the one or more factors associated with the pharmaceutical treatment. In some embodiments, the computerized system is further configured to determine a number of packs of a pharmaceutical treatment required for a patient based on the average dose requirement of the pharmaceutical treatment and the duration of treatment. In some embodiments, the third set of parameters include an offered price per pack of the pharmaceutical treatment and an offered rebate of the pharmaceutical treatment.

In some embodiments, the computerized system is further configured to convert the determined price per pack of the pharmaceutical treatment to a price per patient of the pharmaceutical treatment based on the one or more factors associated with the pharmaceutical treatment. In some embodiments, the computerized system is further configured to compare the expected price of the pharmaceutical treatment to the offered price of the pharmaceutical treatment, in response to determining that the expected price of the pharmaceutical treatment and the offered price of the pharmaceutical treatment are within a predetermined range of each other, provide an agreement signal to the first computing device and the second computing device.

In some embodiments, the computerized system is further configured to provide a disagreement signal to the first computing device and the second computing device, in response to determining that the expected price of the pharmaceutical treatment and the offered price of the pharmaceutical treatment are outside of the predetermined range of each other. In some embodiments, the disagreement signal sent to the first computing device further comprises a suggested expected price of the pharmaceutical treatment based on historical data associated with the first computing device and a difference between the expected price and the offered price. In some embodiments, the disagreement signal sent to the second computing device further comprises a suggested offered price of the pharmaceutical treatment based on historical data associated with the second computing device and a difference between the expected price and the offered price. In some embodiments, the computerized system is further configured to receive an updated expected price of the pharmaceutical treatment from the first computing device, in response to the disagreement signal, and receive an updated offered price of the pharmaceutical treatment from the second computing device, in response to the disagreement signal.

These and other capabilities of the disclosed subject matter will be more fully understood after a review of the following figures, detailed description, and claims. It is to be understood that the phraseology and terminology employed herein are for the purpose of description and should not be regarded as limiting.

BRIEF DESCRIPTION OF DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 8 is an interface depicting a summary of the deal proposal before it is submitted to the pharmaceutical company, in accordance with some embodiments of the disclosure.

DETAILED DESCRIPTION

According to embodiments of the present disclosure, systems and methods are disclosed that accelerate complex decision-making processes between a number of organizations and incorporate elements of problem-solving, negotiation, and cooperation.

Entirely new types of drug therapies are being developed by public research organizations and private sector innovators to combat various illnesses. Scientific breakthroughs in genomics, epigenetics, and system biology are paying off. Drug pipelines are full of breakthroughs including targeted immunotherapy, cell and gene therapy, and others.

However, these new types of drug therapies are unable to reach the market at the same speed as which they are being developed. Typically, negotiation processes between pharmaceutical companies that produce the drugs, and governments (also referred to as payers) that buy the drugs lag behind scientific innovation. Pharmaceutical companies and payers are looking for innovative pricing strategies like indication and value-based pricing for treatment regimens based on new drug therapies. But negotiations between the various parties involved take too long. For combination therapies, if three or more three parties are involved, the negotiations are even more complicated, and often not allowed due to anti-trust concerns.

As a result, there is a logjam of therapies that have been approved by regulators, but not yet reimbursed. Patients are not getting the medicines that they need; companies are not selling their newest therapies; and payers and providers are not able to serve their patients. A new negotiation system is needed that reflects the scientific innovations and the new reality of therapies on the market.

Figure 1:
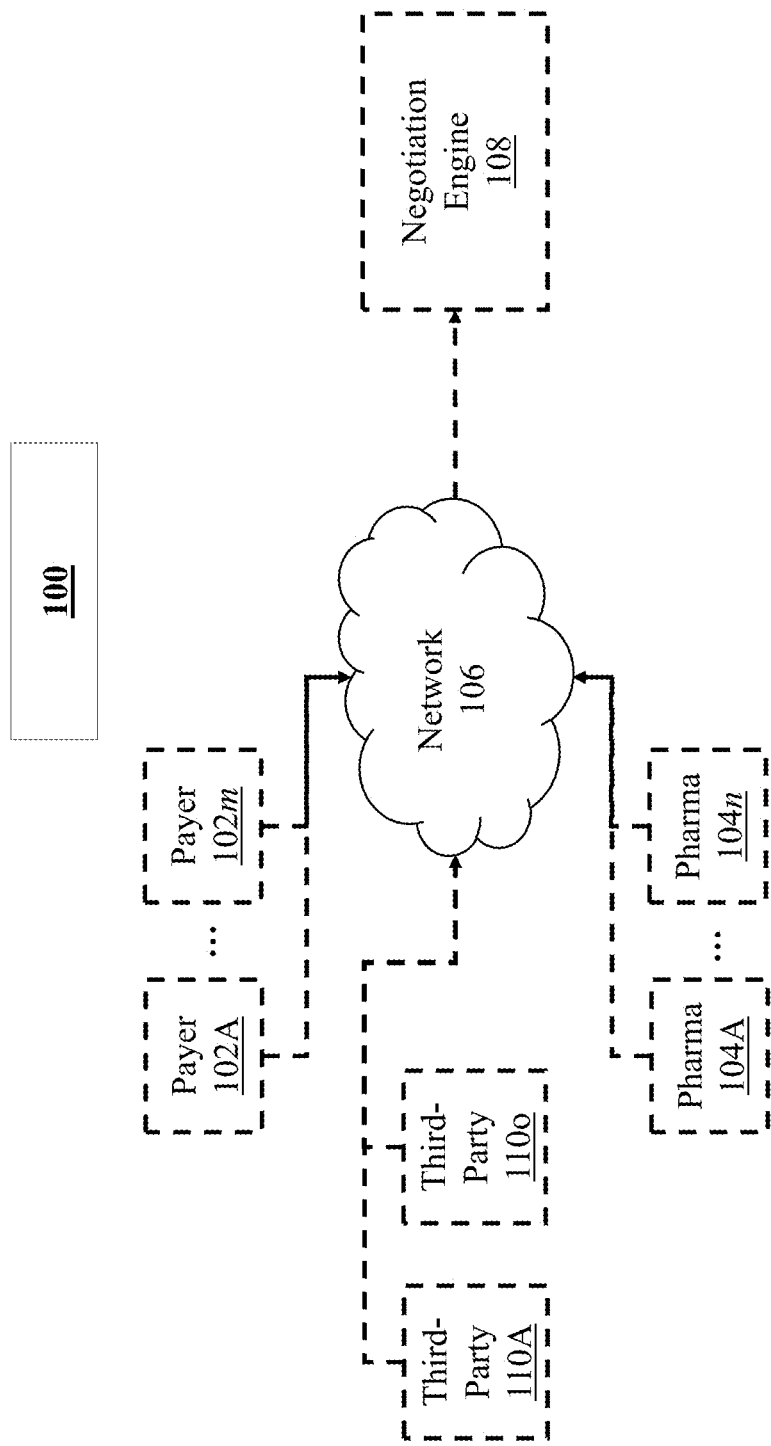
FIG. 1 shows a block diagram of a system 100, in accordance with some embodiments of the disclosure.

FIG. 1 shows a block diagram of a system 100, in accordance with some embodiments of the disclosure. System 100 may include m payer computing devices 102A-102m, n pharmaceutical company computing devices 104A-104n, and o third parties 110A-110o. In some embodiments, each computing device 102A-102m is associated with a different payer, each computing device 104A-104n is associated with a different pharmaceutical company, and each computing device 110A-110o is associated with a different third-party. In some embodiments, more than one user is authorized to access information routed through each of the each of the computing devices 102A-m, 104A-n, and 110A-o. An administrator at each of the computing devices 102A-m, 104A-n, and 110A-o may divide the relevant authorized users associated with the respective computing devices into various teams. This helps to allow an automatic routing of the information directly to the authorized users that associated with the information. In some embodiments, the administrators group the users into logical entities based on the products they may have access to. In some embodiments, a pharmaceutical company associated with one of the computing devices 102A-m may have an oncology team and a cardio-vascular team in the organization associated with the pharmaceutical company. Even within oncology, a team may be responsible for breast cancer products and another one for lung cancer products. In some embodiments, teams may be set up for same product but different indication, for example, Team A of a pharmaceutical company associated with computing device 102A may handle Keytruda for Melanoma and Team B of pharmaceutical company associated with computing device 102A may handle Keytruda for Lung Cancer. Tables 1-3 depict examples of created teams in a pharmaceutical company 102A and a payer 104A and the negotiation is for Product A for Indication A and Product B for Indication A.

TABLE 1

Payer 102A Team
2 Members, 2 Products

| Payer 102A User 1 | Product A (Indication A) |
| Payer 102A User 2 | Product B (Indication A) |

TABLE 2

Pharma 104A Team 1
2 Members, 1 Product

| Pharma 104A User 1 | Product A (Indication A) |
| Pharma 104A User 2 | |

TABLE 3

Pharma 104A Team 2
3 Members, 1 Product

| Pharma 104A User 1 | Product B (Indication A) |
| Pharma 104A User 2 | |
| Pharma 104A User 3 | |

In some embodiments, multiple of the computing devices 102A-m, 104A-n may be part of the same pharmaceutical company or the payer. In some embodiments, as described, these users may be divided into teams for ease of information distribution. In some embodiments, the administrator of the negotiation engine 108 is defines different levels of permissions that may be granted to various users that are part of a pharmaceutical company or a payer. For example, permissions may be based on geographical limitations, and limitations on drug therapy. Thus, a user may have permissions to view all negotiations that are taking place with the government of a particular country, or a particular region. In some embodiments, the permissions may allow a user to view negotiations of a particular pharmaceutical company or a payer. In some embodiments, permissions may include viewing all negotiations without any permission to edit or make any changes to the negotiations. In some embodiments, permissions may include viewing even those parameters of a negotiation that have been hidden from the other negotiating parties. For example, a payer may choose to hide the initial price of a negotiation from a pharmaceutical company, but with the right permissions, a third-party user may be able to view the price of negotiation entered by the payer.

In some embodiments, a set of permissions may be used to create a role. The assignment of permissions may take place dynamically. A role incorporates a set of permissions which could be modified at any point without modifying the role itself. Roles can be created in the system at any given time based on an administrator's decision to have the role, or client's necessity. Some exemplary roles are Admin Read-Only, Admin User, Payer Admin User, Payer User, Payer Read-Only User, Pharma Admin User, Pharma Read-Only User, Pharma User. An Admin Read-Only User may be defined as user without an ability to create/modify/delete any administrator application-based artifacts. An Admin User may be defined as a user with full access to any administrator application artifacts. A Payer Admin User may be defined as payer user who is the "Negotiation Engine Administrator" within the payer's organization. A Payer User may be defined as a payer user with an ability to run negotiations. A Payer Read-Only User may be defined as a payer user with a read only access to the negotiations. Pharma Admin User, Pharma User, and Pharma Read-Only User may be defined similar to their payer counterparts. In some embodiments, Standard Permissions specific to the Payer and Pharma users may be defined. In some embodiments, Advanced Permissions specific to the "Administrator" users of the negotiation engine 108 may be defined.

In some embodiments, government, non-government, donors, hedge-funds, insurance companies, financial institutions, high net worth individuals, or other intermediaries may be an example of a third party, that may step in to guarantee payment for a payer from an emerging market. In some embodiments, a hedge fund may be an example of a third party, that may be willing to buy some of the risk associated with the negotiation between the payer and the pharmaceutical company. In some embodiments, a data provider may be an example of a third-party that may "bid" to provide the data used to clear the payments between the payer and the pharmaceutical company. In the example of FIG. 1, $m$, $n$, and $o$ may be arbitrarily large finite integers greater than or equal to one. The payers and the pharmaceutical companies may be connected to a negotiation engine 108 via a network 106. In some embodiments, network 106 may be any one of a wireless local area network, local area network, Internet, or any other form of network.

The negotiation engine 108 receives and evaluates offers from both parties (the payers 102A-m and the pharmaceutical companies 104A-n). The negotiation engine 108 may be executed and maintained by an administrator not related to the payers 102A-m, the pharmaceutical companies 104A-n, or the third parties 110A-o. The administrator may provide access to the negotiation engine 108 to the pharmaceutical companies and the payers. In some embodiments, the administrator keeps a running record of all of the products that each of the pharmaceutical companies 104A-n are offering at a particular point in time. In some embodiments, the list of products includes a detailed view of the product listing, the product characteristics, as well as a list of product packs applicable for the product with an ability to add new products, modify and delete existing products.

In some embodiments, the administrator also receives a basic set of assumptions, agreed upon by one or more pharmaceutical companies 104A-n and one or more of the payers 104A-m. The basic set of assumptions may include average patient weight, average patient body surface area, date on which the assumption was made. These assumptions may be customized for each product, by including an average number of product packs per year administered to a patient. A product pack is a unit of a product that is determined based on an average dosage administered to a patient within a pre-determined set of time. In some embodiments, the administrator may determine a product pack and a price of the product pack based on a dosing schedule associated with a product. A dosing schedule is received along with information associated with a new product from one of the pharmaceutical companies 102A-m. The dosing schedule includes a start cycle, a cycle length, an end cycle, and dosing for all days in the cycle which consists out number of product administrations per day, as well as the single admin dose. In some embodiments, when adding a new product, a pharmaceutical company may add the new product to a therapy regimen. A therapy regimen may contain one product (monotherapy) or multiple products (combination therapy). At any point, administrator may create a new therapy with attributes such as diagnosis, regimen code, market, therapy type (mono or combination), product 1, product 1 primary pack, product 1 dose calculation method, product 2 (in case of the combination therapy), product 2 primary pack, product 2 dose calculation method.

In some embodiments, the interface of the negotiation engine 108 provided to the payers may be different from the interface of the negotiation engine provided to the pharmaceutical companies. In some embodiments negotiation engine 108 may be hosted on a web server remotely with respect to the payers 102A-m and pharmaceutical companies 104A-n. In some embodiments, the negotiation engine may include different modes of operation. In some embodiments, the negotiation engine may include more than one environment for the users (payers 102A-m and pharmaceutical companies 104A-n). A first mode of operation, also known as a sandbox environment, may be a simulation environment. The sandbox environment is able to replicate the interface presented to both the payers and the pharmaceutical companies. However, access to the sandbox environment is limited to people working at an organization, or people associated with the organization who have been provided access to. The sandbox is only a trial environment and trades proposed in the sandbox environment are only for test purposes and have no consequence.

A second mode of operation, also known as terminal environment, is a real-world environment that may result in binding trades. The terminal environment allows users to express commitments that may be presented to other organizations that may be invited to participate in the negotiation process.

Payer and pharmaceutical data and communications between the payers 102A-m and the pharmaceutical companies 104A-n are preferably encrypted.

Different facets of the interface of the negotiation engine 108 are described with respect to FIGS. 2-10. Any negotiation, or deal for a drug therapy or regimen, may be initiated from the end of the payer, through the payer interface of the negotiation engine. In the payer interface of the negotiation engine, negotiations may be grouped by "indication or disease", as described in more detail below. For example, a payer may open a negotiation for multiple myeloma, and regardless of the therapies used, all negotiations for multiple myeloma will be grouped in the same space. Additionally, a negotiation, or deal for a drug therapy or regimen, may be initiated from the end of the pharmaceutical company, through the pharmaceutical company interface of the negotiation engine. In the interface provided to the pharmaceutical company, negotiations may be grouped by the drugs provided. For example, a pharmaceutical company may group any or all negotiations involving a particular drug (e.g., Keytruda), regardless of the diagnosis for which they might be prescribed. The payers specify negotiation parameters such as contract period, structure, regimen, currency, and pricing units, which are described in greater detail below.

Figure 2:
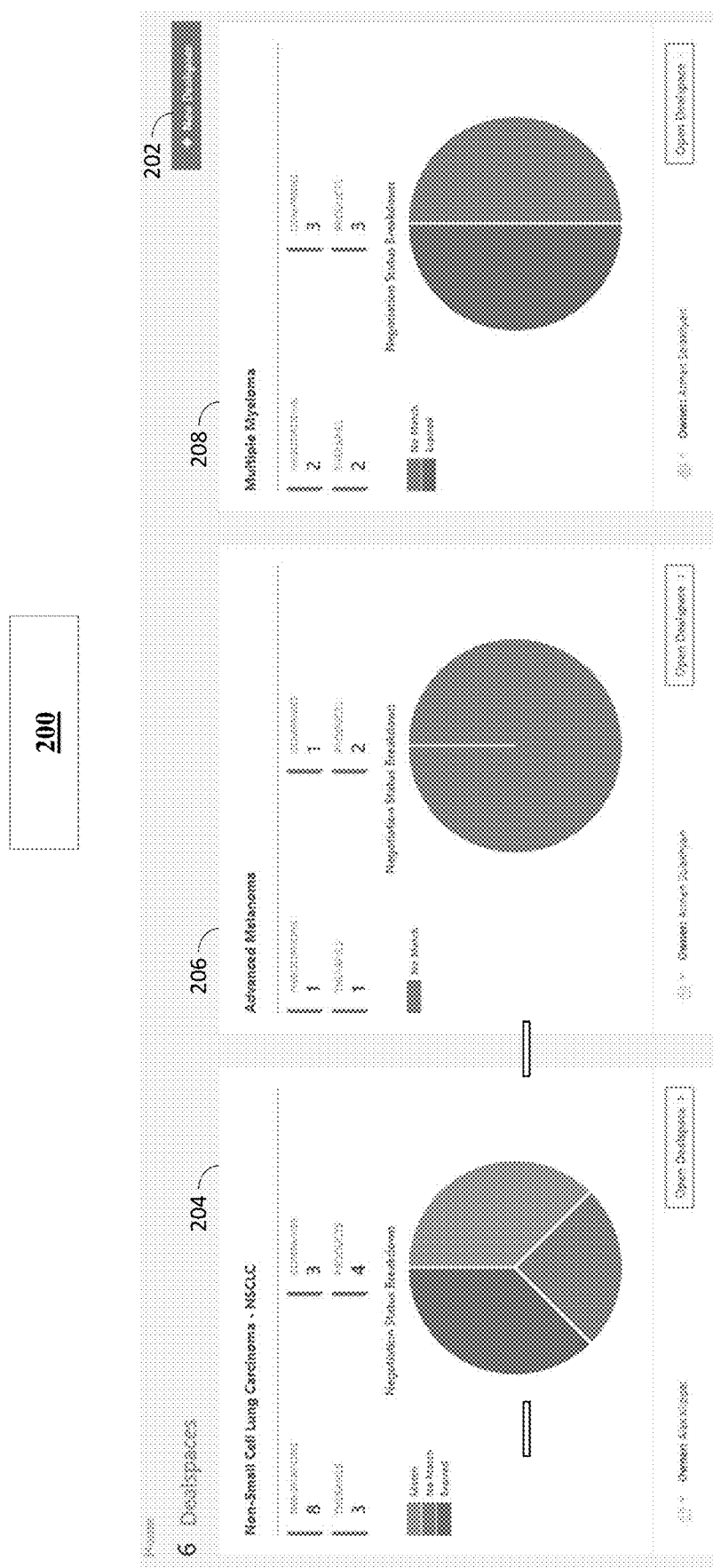
FIG. 2 depicts an interface of the negotiation engine 108 provided to the payer, in accordance with some embodiments of the disclosure.

FIG. 2 depicts an interface of the negotiation engine 108 provided to the payer, in accordance with some embodiments of this disclosure. Any one of the payers 102A-m are able to access the negotiation engine 108 using credentials provided to them by the third party that is responsible for managing the negotiation engine 108. Once the payer logs in to the negotiation engine 108, an interface similar to interface 200 is presented to the payer. Interface 200 includes a button 202 that may be used to initialize a new deal space. Interface 200 also depicts summaries 204, 206, and 208 of all of the deal spaces that are in various stages of progress. A deal space is a collection of ongoing negotiations that have been initiated for a particular diagnosis. As shown in FIG. 2, deal space summary 204 depicts a summary of deals that are in progress for Non-Small Cell Lung Carcinoma. Deal space summary 204 depicts the number of negotiations in progress, the number of companies involved, the number of products in the negotiation, and the number of eligible patients. Similar to deal space summary 204, deal space summaries 206 and 208 depict summaries of ongoing negotiations for Advanced Melanoma and Multiple Myeloma. Deal space summaries 204, 206, and 208 also include information regarding the Owner of the deal space. The Owner of the deal space may be an authorized user in charge of the negotiations related to the identified diagnosis.

Figure 3:
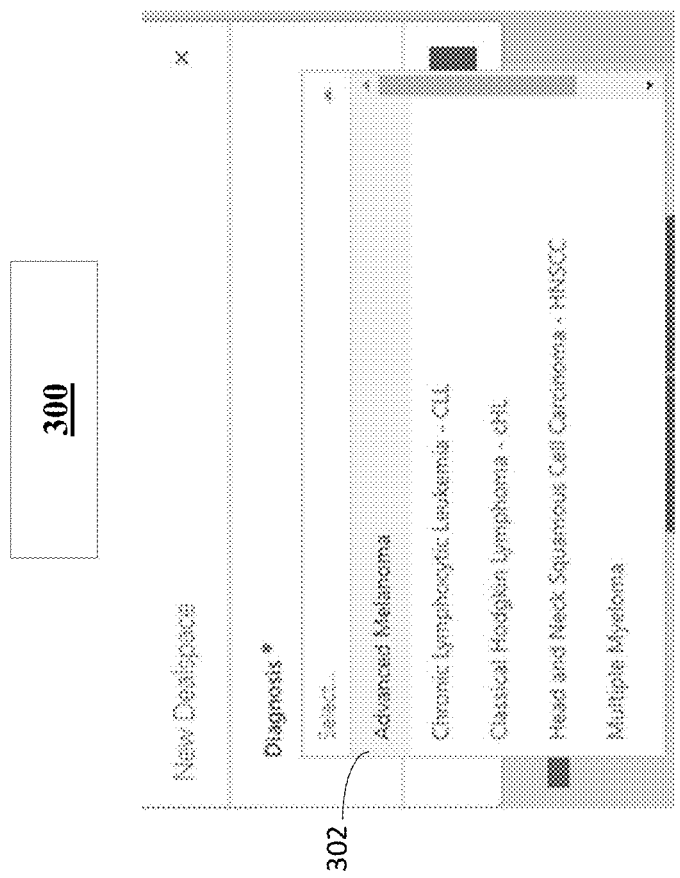
FIG. 3 depicts an interface of creating a new deal space in the negotiation engine, in accordance with some embodiments of the disclosure.

FIG. 3 depicts an interface of creating a new deal space in the negotiation engine, in accordance with some embodiments of this disclosure. Interface 300 depicted in FIG. 3 is generated when a user clicks on button 202 in interface 200 of FIG. 2 to create a new deal space. The first thing needed to open a new deal space is a diagnosis for which a drug therapy is required. In some embodiments, the diagnosis may be selected from the drop-down menu 302 available in the interface 300. In some embodiments, the diagnoses available in the drop-down menu 302 may be provided based on the products and drug therapies that various pharmaceutical companies have made available to the administrator of the database.

Figure 4:
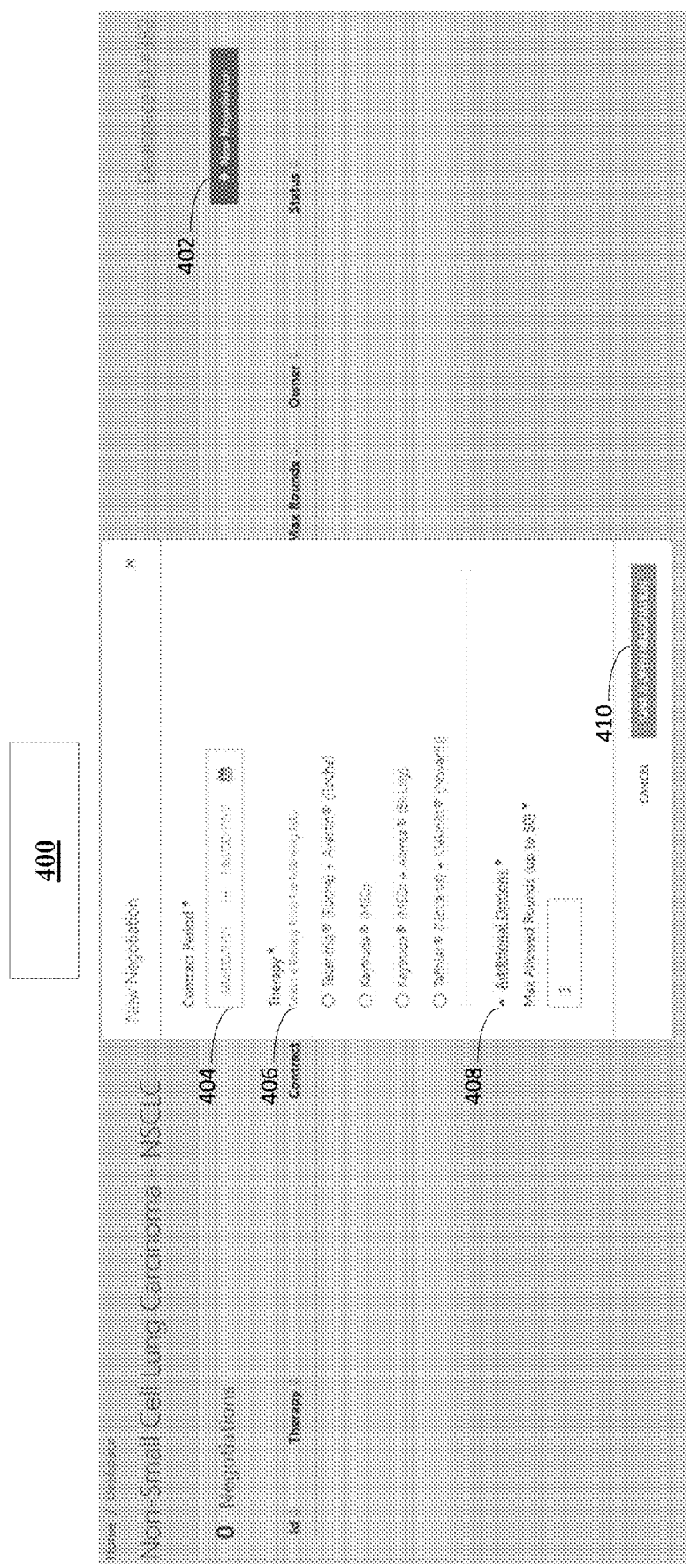
FIG. 4 depicts an interface of creating a new deal within a created new deal space in the negotiation engine, in accordance with some embodiments of this disclosure.

FIG. 4 depicts an interface of creating a new deal within a created new deal space in the negotiation engine, in accordance with some embodiments of this disclosure. Once a new deal space has been created, a user may create a new negotiation within the new deal space by clicking on button 402 of interface 400. In order to begin a new negotiation, the negotiation engine 108 requires certain information that is considered to be the cornerstone of the negotiations. First, the payer should define contract period 404 of the negotiation. In some embodiments, the start and end dates of the contract period 404 may be selected using a calendar functionality implemented in the negotiation engine 108. Second, the payer should select a drug therapy from the list 406 that may be used to treat the selected diagnosis identified by the deal space. List 406 is populated in the interface using the information provided by the various computing devices 104A-n associated with pharmaceutical companies to the administrator. Interface 400 also includes additional options 408. In some embodiments additional options 408 may include an option to specify maximum rounds of negotiations between the payer and the pharmaceutical company. Once all the information has been input, the user may press button 410 to open a negotiation.

Figure 5:
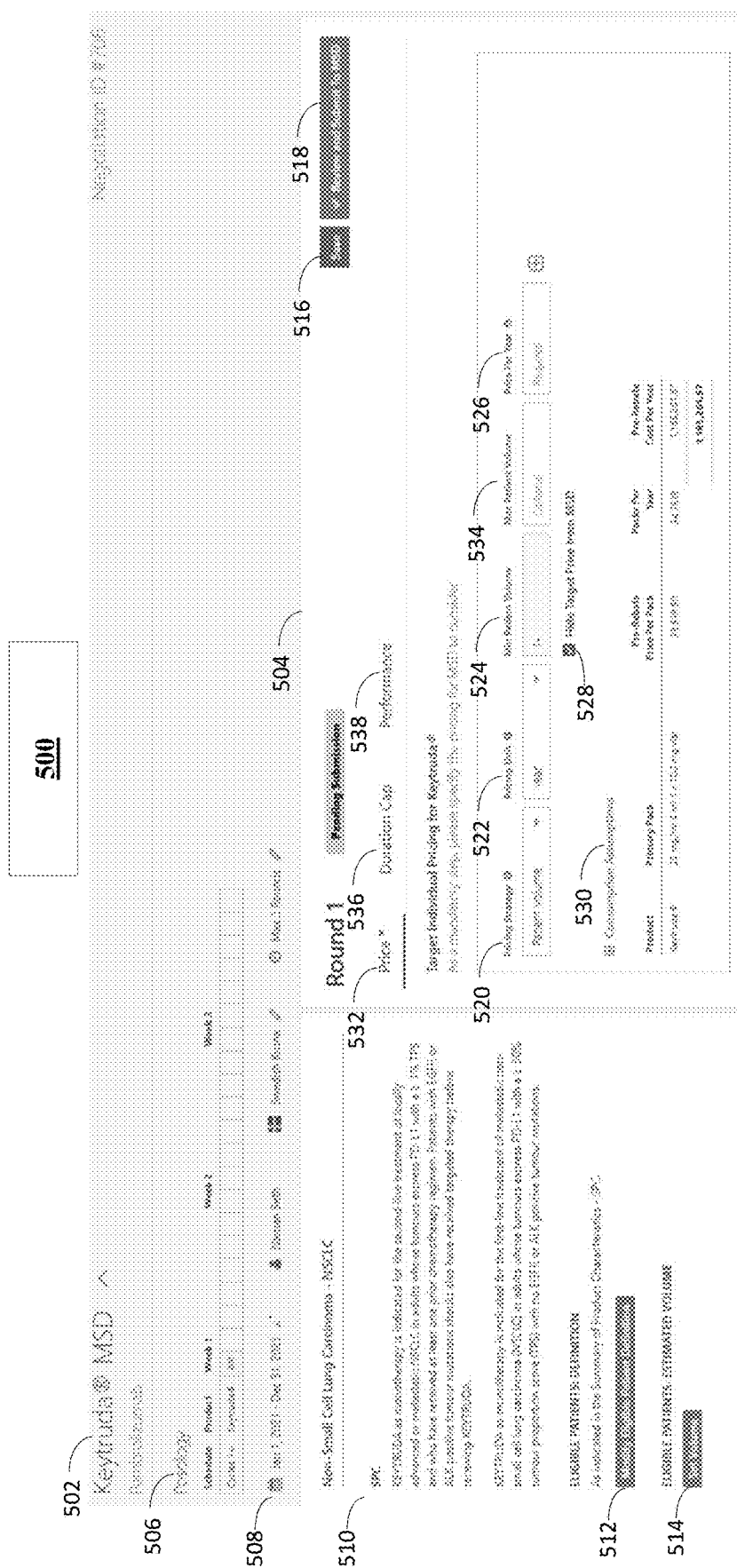
FIG. 5 depicts an exemplary interface of a deal space of the negotiation engine, in accordance with some embodiments of the disclosure.

FIG. 5 depicts an exemplary interface of a deal space of the negotiation engine, in accordance with some embodiments of the disclosure. In some embodiments, interface 500 of the negotiation engine 108 depicts the deal space of Keytruda MSD. The deal space interface 500 includes different sections. Section 502 is a header of the deal space. Section 502 includes a subsection 508 that comprises some of the basic information specified when creating deal space from window 400 of FIG. 4. Section 502 includes a drug therapy for a particular diagnosis. Subsection 508 of section 502 comprises of the selected contract period, name of the person initiating the negotiation, a currency in which the negotiation will be conducted, and the number of rounds specified at the time of creation of the deal space. Each of these options may be modified at any time using the pencil icon depicted on the side of each of the displayed options.

Section 504 of interface 500 depicts an interface to receive a price input to begin a new negotiation. Section 504 includes a pricing tab 532. The pricing tab 532 includes a pricing unit drop-down menu 522 that includes a plurality of options, for example, Year Price, Quarter Price, Month Price, and Cycle Price. Cycle Price reflects the treatment of a single patient for one cycle. In some embodiments, one cycle of treatment for a patient is 3 weeks. There might be a 4th week where the patient does not consume any medication. In some embodiments, as the cycle progresses, the dosage of the medication may change. Month Price reflects the treatment of a single patient for one month. Quarter Price reflects the treatment of a single patient for one quarter. Year Price reflects the treatment of a single patient for one year.

Pricing strategy drop-down 520 includes different patient strategies for pricing. In some embodiments, the payer may add a preference for a particular therapy over others, and the interface may allow the payer to specify multiple preferences. A first strategy of pricing is Patient Volume. Patient Volume Pricing is based on the number of patients treated. Because Patient Volume Pricing is based on the number of patients, price provisions may differ based on the total volume of patients treated. Input fields 524 and 534 depict inputs for receiving for pricing details for the Patient Volume. At 524, the payer may specify a minimum patient volume. At 534, the payer may specify a maximum patient volume, and at 526, the payer specifies a price point for the entered patient volume. In some embodiments, if price doesn't change depending on volume, the max patient volume field can be left empty. In some embodiments, the payer may wish to break down the pricing patient volume. In such cases, the payer may enter patient volume breaks and corresponding new price for volume dependent pricing proposals. At 528, the payer has the option to "Hide Target Price" from the pharmaceutical company. In some embodiments, the option to hide the target price may be a global setting or an individual setting. For example, in some countries all data, or specific data will always be hidden, or always visible, and in other countries the payers or pharmaceutical companies may be free to choose what they want to do. Selection of this option will hide the target (combination) price will be hidden from the other negotiation parties. In some embodiments, an additional provision in the Patient Volume pricing provision may be defined. This additional provision may be a "Duration Cap." The interface for the "Duration Cap" may be initiated by pressing the button 536. This duration cap rebate allows for additional provisions on top of volume provisions (e.g. in the case of expected market share uncertainty). The interface is described in more detail in FIG. 6.

A second pricing strategy in the drop-down menu 520 is a Treatment Duration Price pricing strategy. A Treatment Duration Pricing Strategy is based on how long a patient is treated. As a consequence, the price of the treatment strategies will be different for each patient based on how long they have been in treatment. In some embodiments, duration of the treatment may be broken down into Year, Quarter, Month, and Cycle. In addition to volume breaks, that is also available in the Patient Volume pricing strategy, allows for an option of duration break Interface 500 of FIG. 5 includes a Performance tab 538 next to the Duration Cap 536 tab 536. The Performance tab specifies price provisions can be made based on (treatment) performance. The interface for the performance tab is described in more detail in FIG. 7.

Section 510 of interface 500 of FIG. 5, includes a brief description of the drug therapy that is the basis of negotiation. This brief description is often referred to as SPC (summary of product characteristics). Part of the SPC includes a description of patients eligible for the drug therapy. In some embodiments, the SPC is information provided to the administrator of negotiation engine 108 by the pharmaceutical company at the time of creation of this drug therapy. In some embodiments, this section 510 includes a subsection 512 where a payer is able to modify the eligibility criteria of patients for this drug therapy. In some embodiments, section 510 includes a subsection 514 where the payer is able to set an estimated volume of patients that will be provided with this drug therapy.

Section 506 of interface 500 visualizes the dosage schedule of the drug therapy when it is administered to a patient. In some embodiments, dosing schedule consists of 1 or many dosing periods with each period representing a changed dose for at least one product in the therapy. In some embodiments, the dosing schedule is provided to the administrator when the drug therapy is added to the negotiation 108. In some embodiments, the dosage schedule setup modal allows user to specify a start cycle end cycle (or open-ended cycle), a cycle length, name override (by default name is being generated from the cycle start and end, i.e. Cycle 1-3). Dosing for all days in the cycle which consists out number of product administrations per day, as well as the single admin dose.

Section 530 of interface 500 displays the consumption assumptions for the selected drug therapy. Section 530 of consumption assumption has multiple purposes. Firstly, section 530 visualizes the primary pack for each of the products part of the negotiation. The concept of the primary pack is common in the industry to negotiate pricing for a specific pack and derive the prices of the other packs based on algebraic formula. Consumption assumption 530 is able to visualize the pre-rebate (list) price for each of the products part of the negotiation. A link is exposed for the user to find out the nature of the price (i.e. the date and the pricing source as depicted to the right). The list prices are sourced from the known and trusted pricing sources specific to a market (country). Consumption assumption 530 visualizes the average number of packs consumed by a single patient if given the product as part of the combination therapy for a given period. Using this information, the consumption assumption section 530 visualizes the cost of a treatment of a single patient for a given period (year in this example) for each of the products part of the negotiation as well as total cost of the therapy if zero rebate was offered. Finally, consumption assumption section 530 is able to connect the pricing unit 532 with the period specified in the consumption assumption period. In some embodiments, if the user wants to negotiate a monthly rebate, the consumption assumption section 530 will reflect monthly numbers.

Negotiation engine 108 includes a translator to calculates the average number of packs a single patient would be administered for a given period. By having that number the administrator can easily translate the period prices to the pack prices and vice versa. These are the numbers that are shown in consumption assumption section 530.

Figures 6, 7:
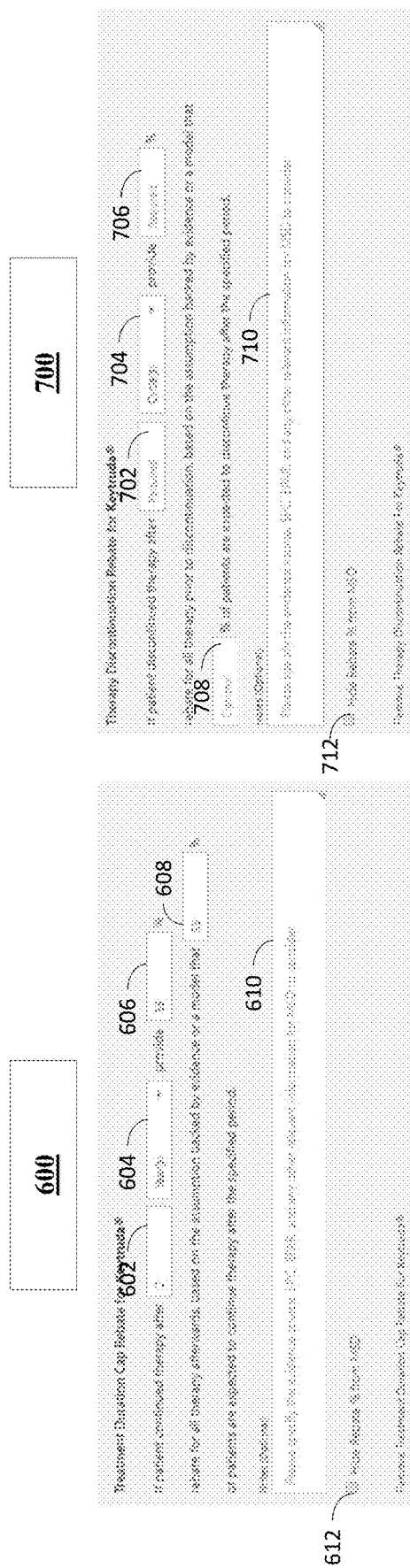
FIG. 6 depicts an interface of a "Duration Cap Rebate" as initiated from interface 500 of FIG. 5, in accordance with some embodiments of the disclosure.
FIG. 7 depicts an interface of "Therapy Discontinuation Rebate" as initiated from interface 500 of FIG. 5, in accordance with some embodiments of the disclosure.

FIG. 6 depicts an interface of a "Duration Cap Rebate" as initiated from interface 500 of FIG. 5, in accordance with some embodiments of the disclosure. Interface 600 of FIG. 6 receives input that requests price rebates (from 1-100%) for patients in input field 606, based on the evidence that a certain proportion of the patients specified in input field 608 are expected to continue therapy after the specified period specified in input fields 602 and 604. The payer has an option to specify to define their inputs received in interface 600 in the "Notes" section 610. The payer also has the option of hiding this rebate specified from the pharmaceutical company by selecting option 612.

FIG. 7 depicts an interface of "Therapy Discontinuation Rebate" as initiated from interface 500 of FIG. 5, in accordance with some embodiments of the disclosure. The therapy discontinuation rebate interface is initiated from the Performance tab of interface 500 of FIG. 5. In some embodiments, pricing provisions may be made based on the performance of the drug regimen. Interface 700 of FIG. 7 receives input that requests price rebates (from 1-100%) for patients in input field 706, based on the evidence that a certain proportion of the patients specified in input field 708 are expected to discontinue therapy due to side effects/ toxicity or lack of response to a specific regimen after the specified period specified in input fields 902 and 704. The payer has an option to specify to define their inputs received in interface 900 in the "Notes" section 710. The payer also has the option of hiding this rebate specified from the pharmaceutical company by selecting option 712.

Figure 8:
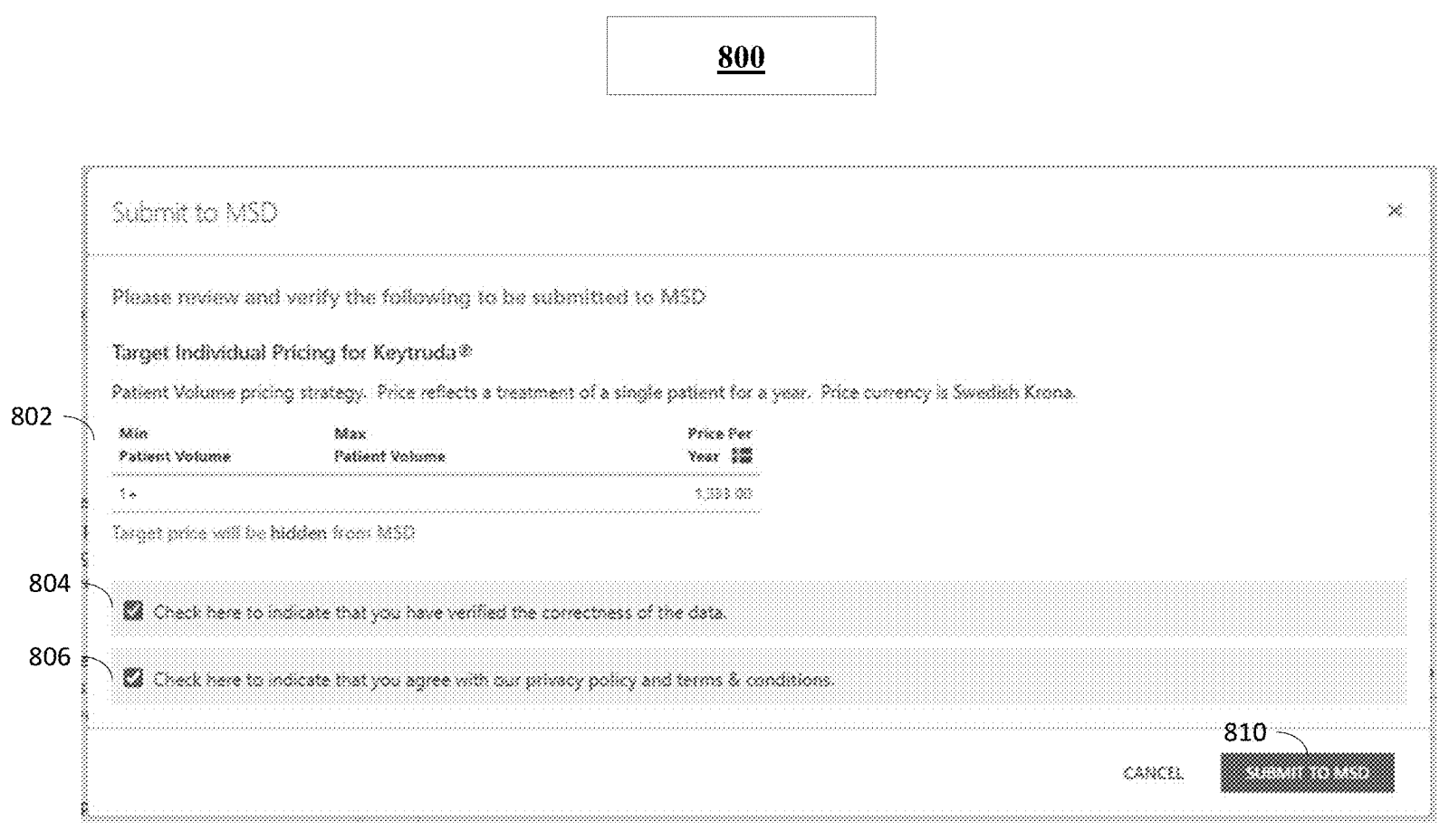

Once the payer has specified all the required information in the interfaces presented in FIG. 2-7, the payer may submit his proposal to the pharmaceutical company for consideration. In some embodiments, the payer may save the current state of the negotiation input and come back to finalize the negotiations by pressing the Save button 516. The payer may begin the submission by pressing the submit button 518 in interface 500 of FIG. 5. Before the payer submits the contingent commitments, a pop-up window similar to the interface 800 of FIG. 8 will be displayed to the payer. FIG. 8 is an interface depicting a summary of the deal proposal before it is submitted to the pharmaceutical company, in accordance with some embodiments of the disclosure. Section 802 of interface 800 of FIG. 8 summarizes the pricing strategy, pricing unit, and the pricing currency as specified in the interface of FIG. 5. Check-boxes 804 and 806 are present to ensure that the accuracy and correctness of the data and that the privacy agreement has been acknowledged. Once the payer confirms the information and accepts the privacy policies, the pricing proposal may be submitted to the other negotiating parties by pressing button 808

Figure 9:
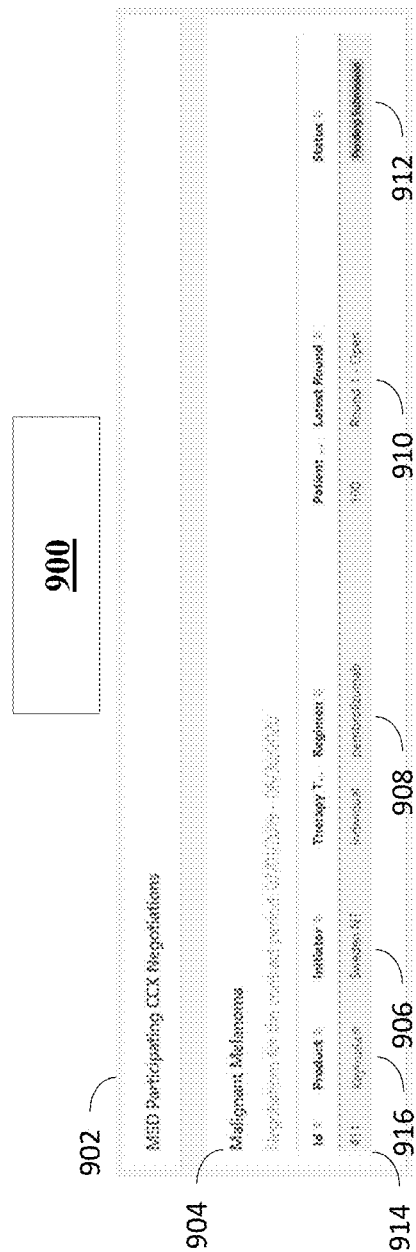
FIG. 9 depicts an interface of the negotiation engine provided to a pharmaceutical company, in accordance with some embodiments of this disclosure.

FIG. 9 depicts an interface of the negotiation engine provided to a pharmaceutical company, in accordance with some embodiments of this disclosure. Any one of the pharmaceutical companies 104A-n are able to access the negotiation engine 108 using credentials provided to them by the third party that is responsible for managing the negotiation engine 108. Once the pharmaceutical company logs in to the negotiation engine 108, an interface similar to interface 900 is presented to the pharmaceutical company. Interface 900 has a header 902 that depicts the negotiations that the pharmaceutical company is involved in. Section 904 organizes by diagnosis, the negotiations that the pharmaceutical company is invited to participate in. As shown in FIG. 9, record 914 summarizes a negotiation proposed by an initiator 914 for a diagnosis specified by 904. Record 914 depicts a negotiation for a product 916 initiated by initiator specified in 906. The record 914 also specifies the regimen 908, the number of rounds 910 the negotiation has gone through, and the current status of the negotiation 912.

Figure 10:
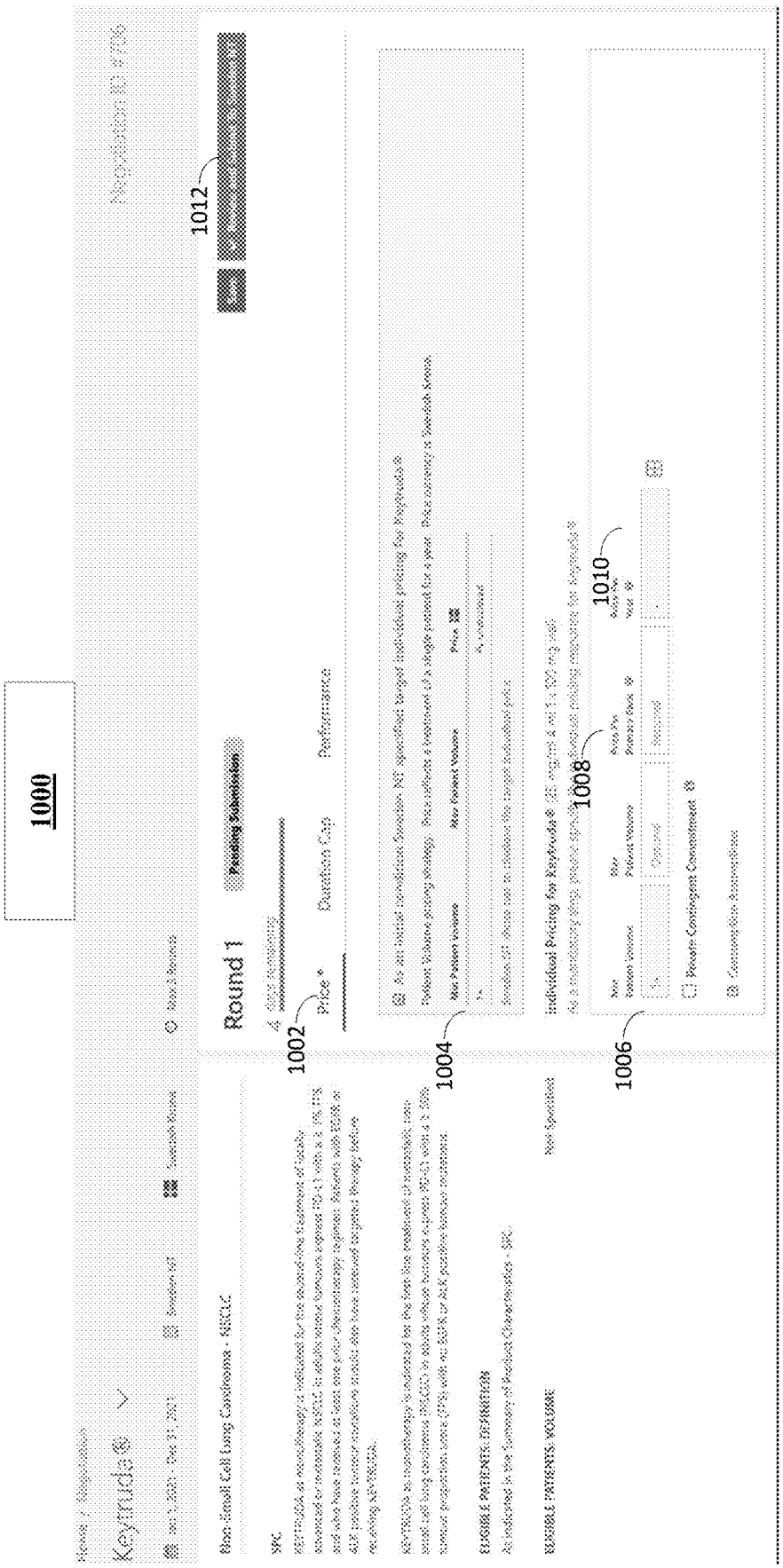
FIG. 10 depicts an interface presented to the pharmaceutical company to respond to a proposed negotiation, in accordance with some embodiments of the disclosure.

FIG. 10 depicts an interface presented to the pharmaceutical company to respond to a proposed negotiation, in accordance with some embodiments of the disclosure. Interface 1000 of FIG. 10 is similar to interface 500 of FIG. 5 except in the pricing section 1002. Pricing section 1002 has a subsection 1004 that displays the initial negotiating offer for the drug therapy as proposed by the payer. In some embodiments, if the payer has decided to hide the initial offering price of the drug therapy and related parameters, the price section of subsection 1004 will say "undisclosed."

Subsection 1006 of Pricing section 1002 receives the offering price of the drug therapy from the pharmaceutical company. For the convenience of the pharmaceutical company, negotiation engine 108 is able to receive the price of the drug therapy in price per primary pack in field 1008. Using the translator, consumption assumptions and the dosage schedules described with respect to FIG. 5, the negotiation engine 1008 is able to convert the price per pack offered by the pharmaceutical company to a price per year in field 1010. This price per year is sent to the payer so that in cases of multiple drug therapies, the payer is able to calculate a comprehensive cost of a drug regimen. Once the pharmaceutical company has entered its offering price for the drug therapy the payer is interested in, the pharmaceutical company is able to submit their price to the payer by pressing button 1012.

Figure 11:
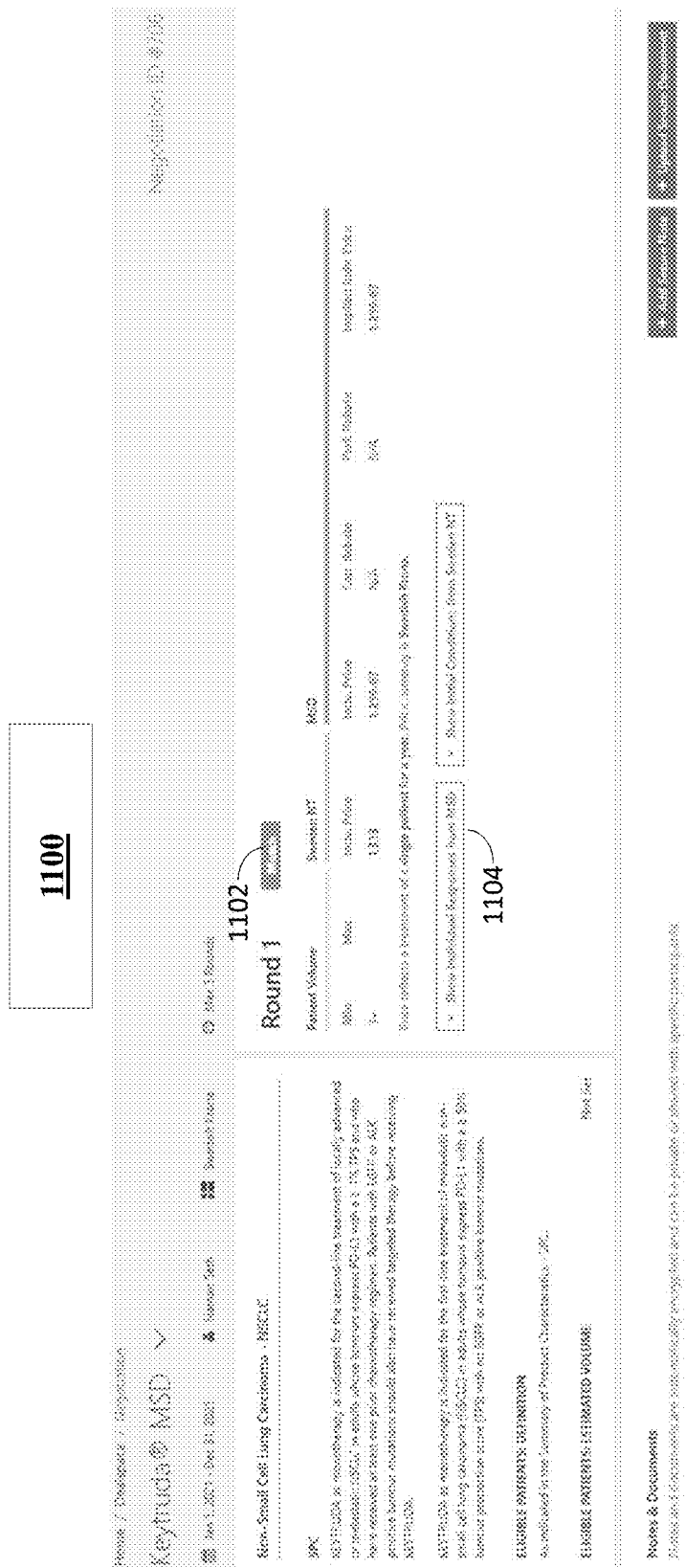
FIG. 11 depicts an interface presented to the payer during a negotiation, in accordance with some embodiments of the disclosure.

FIG. 11 depicts an interface presented to the payer during a negotiation, in accordance with some embodiments of the disclosure. Interface 1100 of FIG. 11 is a modified version of the interface 500 of FIG. 5. Once all the parties involved in a negotiation have entered their proposals, the first round of negotiation is considered closed. Interface 1100 includes an indicator 1102 that displays an evaluation of the proposals to determine whether there is an overlap between the proposals, or there is no match between the proposals. In some embodiments, when there is no match between proposals, the interface 1100 of negotiation engine 108 may include a color scale (red yellow green) indicator in place of indicator 1102 with a slider of where the negotiation stands as far as likelihood of success. In some embodiments, the color scale may not be a single color, but a scale (more like an analog thermometer instead of a digital one). changing different elements of the negotiation (price, volume, performance provisions, etc.) could have an impact on where the marker is on the scale and change it at different rates. For example, the thresholds may have a randomly generated fudge factor, so negotiation parties may not figure out what is happening in the background. If the payer's price is $100 and the pharmaceutical company's price is $110, then the color scale in the interface of the pharmaceutical company of the negotiation engine 108 may be green (based on the assumption both will go down in price). Similarly, if the pharmaceutical company lists its price as $120 then the color scale is yellow, and if the pharmaceutical company's price is $130, the color scale is red.

In some embodiments, if the initiator of the negotiation is the payer, the interface 1100 of the negotiation engine 108 shows a pricing recommendation section (not shown) in a pricing commitment tab above or below the pricing provision. In some embodiments, the pricing recommendation section includes one or multiple price tiers along with the graphical representation of a probability of success. In some embodiments, the probability of success may be based on a contingent commitment specified by the payer. For example, the contingent commitment may specify a limit of a matching percentage, or a percentage of other's price. In some examples, the contingent price may be based on dollar amounts. In some examples, the initiator of a negotiation may have the ability to introduce a commitment based on commitments from the opposing party of the negotiation. In some embodiments, in case the negotiation engine 108 determines that the pricing specified in the previous round should not change "price should not be changed" will appear along with a probability of success widget, in the pricing commitment tab, if the payer keeps the same price. The probability of success could be different from the previous round with the assumption that there is a certain probability that the pharmaceutical company will accept the nudging recommendation.

In some embodiments, if the initiator of the negotiation is payer the interface of the negotiation engine 108 associated with the payer shows a treatment continuation recommendation section in the Duration Cap tab above or below the treatment continuation commitment. In some embodiments, this would include information such as number of cycles after which the treatment continuation rebate applies, rebate percentage, percentage of the patient population expected to continue the therapy, and a probability of success widget. In some embodiments, if the nudging algorithm of the negotiation engine 108 determines that the treatment continuation information specified in the previous round should not change, in the Duration Cap tab "treatment continuation commitment should not be changed" message will appear along with the probability of success widget. In some embodiments, the probability of success could be different from the previous round with the assumption that there is a certain probability that the payer will accept the nudging recommendation. In some embodiments, the nudging algorithm of the negotiation engine 108 will determine that the therapy continuation commitment should be removed and incorporated into the pharmaceutical company's pricing commitment. In this case an adequate message would be displayed to the pharmaceutical company on both Pricing and treatment Duration Cap tabs along with the probability of success widget.

In some embodiments, if the initiator of the negotiation is payer, the interface of the negotiation engine 108 shows a therapy discontinuation recommendation section in the Performance Tab above or below the therapy discontinuation commitment. In some embodiments, this would include information such as number of cycles after which the therapy discontinuation rebate applies, rebate percentage, percentage of the patient population expected to discontinue the therapy, probability of success widget. In some embodiments, if the nudging algorithm of the negotiation engine 108 determines that the therapy discontinuation information specified in the previous round should not change, in the Performance Tab "therapy discontinuation commitment should not be changed" message will appear along with the probability of success widget. In some embodiments, the probability of success could be different from the previous round with the assumption that there is a certain probability that the payer will accept the nudging recommendation. In some embodiments, it is possible that the nudging algorithm will determine that the therapy discontinuation commitment should be removed and incorporated into the pharmaceutical company's pricing commitment. In some embodiments, an adequate message would be displayed to the pharmaceutical company on both pricing and performance tabs along with the probability of success widget.

In some embodiments, the nudging algorithm of the negotiation engine 108 would detect the payer should change the pricing strategy or the pricing unit in the next round. The payer interface will display such message to the user just below the Round section of the screen.

In some embodiments, the probability of success widget described at the round level displays an overall success probability of the round. In some embodiments, the probability of success widget at the commitment level, e.g., pricing/therapy continuation/therapy discontinuation is a percentage widget which displays a delta success factor each commitment recommendation attributes to the overall negotiation success probability.

The platform will indicate/whether a match has been achieved or not (based purely on price). It is possible that a price is acceptable to all parties, but includes price provisions which depend on actual patient treatment durations and responses. More information regarding the price provided by the other involved parties is available if the payer decided to click the button 1104. The interface for the pricing model provided by the pharmaceutical company is described in more detail in FIG. 11.

In case there is no match, the negotiation engine 108 will distinguish between deal-components where there might be a match and deals where there is no match. In some embodiments, the negotiation engine will nudge both the parties to a more equitable solution.

Figure 12:
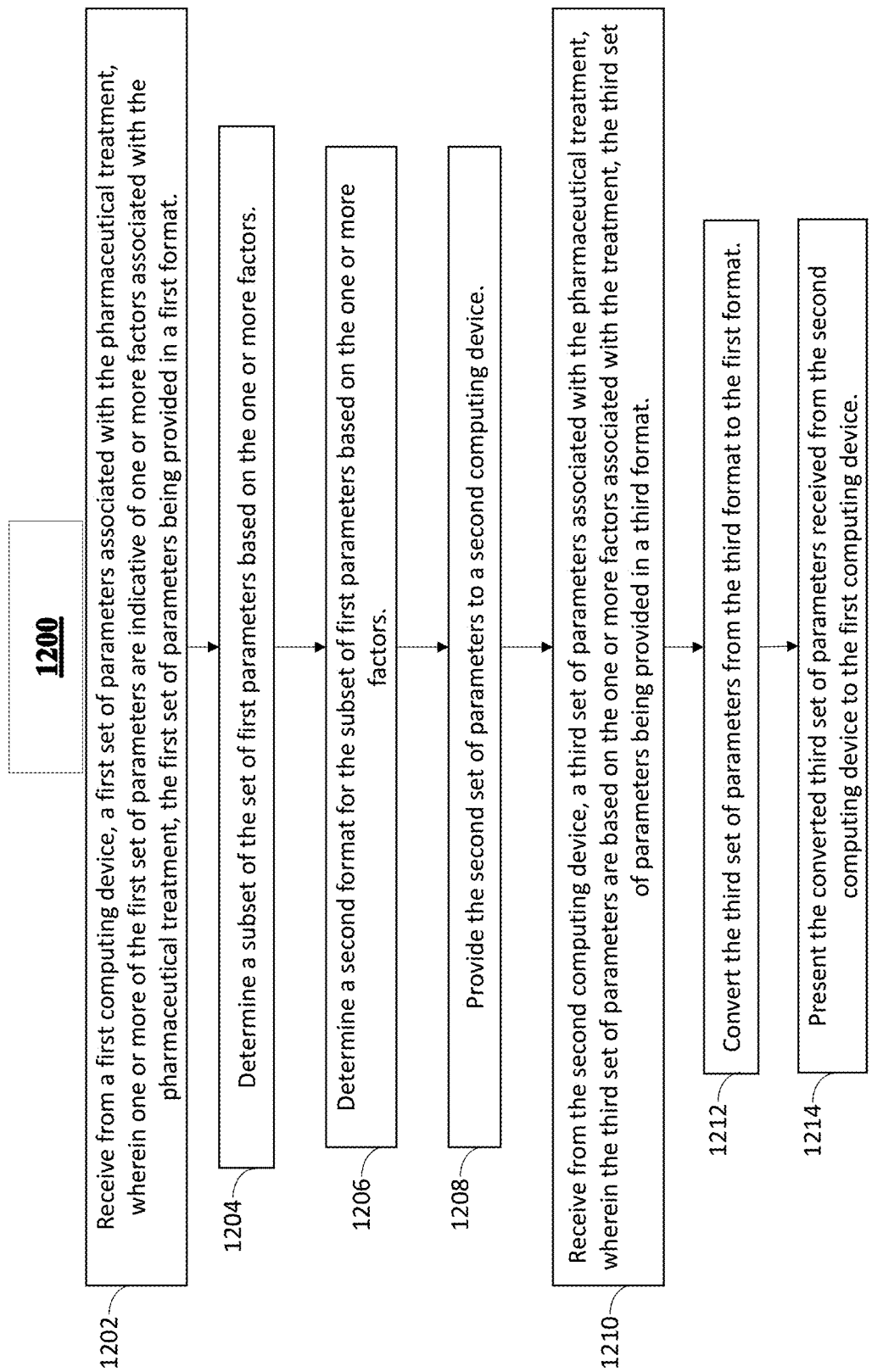
FIG. 12 depicts an illustrative flowchart of a process of a negotiation between two parties, in accordance with some embodiments of the disclosure.

FIG. 12 depicts an illustrative flowchart of a process of a negotiation between two parties, in accordance with some embodiments of the disclosure.

At 1202, the negotiation engine 108 receives from a first computing device, a first set of parameters associated with the pharmaceutical treatment, wherein one or more of the first set of parameters are indicative of one or more factors associated with the pharmaceutical treatment, the first set of parameters being provided in a first format. In some embodiments, as shown in FIGS. 3-7, the first set of parameters associated with a negotiation may comprise information like the name of the drug, dosage schedule, duration of drug therapy, number of patients eligible for the drug therapy, a price of the drug therapy, an expected rebate on the price of the drug therapy, a pricing strategy for the drug therapy. In some embodiments, some of this information, e.g., name of the drug, dosage schedule, criteria for eligible patients, may be entered by the pharmaceutical company when creating the drug therapy in negotiation engine 108. In some embodiments, some other information may be received from the payer such as number of eligible patients, duration of the drug therapy, expected price, and expected rebate on the price.

At 1204, the negotiation engine 108 determines a subset of the set of first parameters based on the one or more factors. In some embodiments, as shown with respect to FIGS. 5-7, the payer may decide to hide some parameters from the pharmaceutical company when creating the negotiation proposal. In such embodiments, the payer may ask the negotiation engine 108 to hide the price of the drug by selecting option 528 from interface 500, and the expected rebate by selecting option 612 of interface 600, and option 712 of interface 700 from the pharmaceutical company.

At 1206, the negotiation engine 108 determines a second format for the subset of first parameters based on the one or more factors. In some embodiments, the price entered by the pharmaceutical company for the drug therapy may be in per person terms. However, the pharmaceutical companies prefer to receive and provide prices in per pack terms. Using the information like dosage schedule, and primary pack size, that are provided by the pharmaceutical company when creating a drug therapy, the negotiation engine 108 may convert the price per patient (a first format) received from the payer to a price per primary pack (second format).

At 1208, the negotiation engine 108 provides the second set of parameters to a second computing device. The negotiation engine 108 may provide the modified received parameters to the pharmaceutical company for their input.

At 1210, the negotiation engine 108 receives from the second computing device, a third set of parameters associated with the pharmaceutical treatment, wherein the third set of parameters are based on the one or more factors associated with the treatment, the third set of parameters being provided in a third format. In some embodiments, once the parameters are provided to the pharmaceutical company, the pharmaceutical company is able to review information to provide their own input for the pricing of the drug therapy, that is requested by the payer. In some embodiments, the pharmaceutical company may have access to information from the payer when making the decision, and in some cases, that information may be hidden from the pharmaceutical company. The pharmaceutical company will stall have access to certain parameters certain basic parameters such as duration of the drug therapy, number of eligible patients, etc. that will help the pharmaceutical company to provide their price for the drug therapy.

At 1212, the negotiation engine 108 converts the third set of parameters from the third format to the first format. In some embodiments, the payer may enter the price of the drug therapy in their preferred format (per primary pack terms), which are then converted to the preferred format of the payers (per person terms) using the dosage schedule, primary pack size and duration of the drug therapy.

At 1214, the negotiation engine 108 presents the converted third set of parameters received from the second computing device to the first computing device. In some embodiments, the information received from the pharmaceutical company, once modified is sent to the payer for their review. In some embodiments, the negotiation engine 108 may provide indicators based on the difference between the process provided the payer and the pharmaceutical company, to highlight the status of the negotiation.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local-area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, can readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter can be made without departing from the spirit and scope of the disclosed subject matter, which is limited only by the claims which follow.

What is claimed:

1. A computerized system for negotiating a purchase of a pharmaceutical treatment between a provider of the pharmaceutical treatment and a purchaser of the pharmaceutical treatment, comprising:
   a memory; and
   a processor communicatively coupled to memory, wherein the processor is configured to:
      receive one or more assumptions associated with a patient agreed upon by the provider and the purchaser, wherein the purchaser of the pharmaceutical treatment comprises a plurality of purchasers, wherein the one or more assumptions include an average patient body surface area, an average patient weight, and a date associated with the agreed upon assumptions;
      cause display, at a first computing device, a first graphical user interface with a first user input field;
      receive, over a network and via the first user input field on the first graphical user interface, an offer to purchase the pharmaceutical treatment comprising a first set of parameters, wherein the first set of parameters comprises a number of patients eligible for the pharmaceutical treatment, an expected rebate, and an offer to purchase price including a price of the pharmaceutical treatment in a first format, wherein the first format includes the expected price of the pharmaceutical treatment being a price per patient;
      transform the received first set of parameters to a second set of parameters, wherein transforming the first set of parameters to the second set of parameters includes determining a subset of the set of first parameters based on one or more patient assumption factors, wherein determining the subset of the set of first parameters further comprises excluding one or more parameters of the first set of parameters based on an indication to hide the one or more parameters to adhere to a geographical limitation;
      determine a second format for the second set of parameters, wherein the second format includes the expected price of the pharmaceutical treatment being a price per pack for the pharmaceutical treatment;
      cause display, at a second computing device, a second graphical user interface including the second set of parameters that adhere to the geographical limitation, wherein the second set of parameters displayed to each of the plurality of purchasers is different based on the geographical limitation associated with each of the plurality of the purchasers;
      receive, over the network and via a second user input on the second graphical user interface, an offer to provide the pharmaceutical treatment comprising a third set of parameters, the third set of parameters being provided in a third format, and wherein the third set of parameters include an offer to provide price, the offer to provide price including an offered price per pack of the pharmaceutical;
      convert the third set of parameters from the third format to the first format,
      wherein converting the third set of parameters comprises converting the price per pack of the pharmaceutical treatment to the first format comprises converting the determined price per pack of the pharmaceutical treatment to a price per patient of the pharmaceutical treatment;
      determine a probability of success of a negotiation between the purchaser and the provider, wherein the probability of success is based upon a percentage associated with a difference between the offer to purchase price and the offer to provide price; and
      cause display, at the second computing device, a third graphical user interface including the third set of parameters and a recommendation to the purchaser or the provider based on the probability of success, the recommendation including a recommended adjustment for a subsequent round of negotiation.

2. The computerized system of claim 1, wherein the number of patients eligible for the pharmaceutical treatment may be one.

3. The computerized system of claim 1, wherein the first set of parameters comprises a maximum number of rounds of negotiations.

4. The computerized system of claim 1, wherein the pharmaceutical treatment comprises multiple therapies that can be used to treat a same disease or indication.

5. The computerized system of claim 1, wherein the processor is configured to provide a platform for a binding negotiation and a platform for a simulated negotiation.

6. The computerized system of claim 1, wherein the indication to hide the one or more parameters is based on a country-specific rule.

7. The computerized system of claim 1, wherein the probability of success is also based upon one or more of a therapy continuation factor and therapy discontinuation factor.

8. The computerized system of claim 1, wherein the pharmaceutical treatment includes one or more products, the provider of the pharmaceutical treatment includes a plurality of providers, each of the plurality of providers associated with at least a portion of the one or more products.

9. The computerized system of claim 8, wherein the purchaser of the pharmaceutical treatment comprises a plurality of purchasers, each of the purchasers associated with at least a portion of the offer to provide price.

10. The computerized system of claim 1, wherein the purchaser of the pharmaceutical treatment comprises a plurality of purchasers and the second set of parameters displayed to each of the plurality of purchasers adheres to an anti-trust regulation.

11. The computerized system of claim 1, wherein the provider of the pharmaceutical treatment comprises a plurality of providers and the third set of parameters displayed to each of the plurality of providers adheres to an anti-trust regulation.

12. A computerized system for negotiating a purchase of a pharmaceutical treatment between a provider of the pharmaceutical treatment and a purchaser of the pharmaceutical treatment, comprising:
   a memory; and
   a processor communicatively coupled to memory, wherein the processor is configured to:
      receive one or more assumptions associated with a patient agreed upon by the provider and the purchaser, wherein the provider of the pharmaceutical treatment comprises a plurality of providers, wherein the one or more assumptions include an average patient body surface area, an average patient weight, and a date associated with the agreed upon assumptions;

cause display, at a first computing device, a first graphical user interface with a first user input field;
receive, over a network and via the first user input field on the first graphical user interface, an offer to purchase the pharmaceutical treatment comprising a first set of parameters, wherein the first set of parameters comprises a number of patients eligible for the pharmaceutical treatment, an expected rebate, and an offer to purchase price including a price of the pharmaceutical treatment in a first format, wherein the first format includes the expected price of the pharmaceutical treatment being a price per patient;
transform the received first set of parameters to a second set of parameters, wherein transforming the first set of parameters to the second set of parameters includes determining a subset of the set of first parameters based on one or more patient assumption factors, wherein determining the subset of the set of first parameters further comprises excluding one or more parameters of the first set of parameters based on an indication to hide the one or more parameters to adhere to a geographical limitation;
determine a second format for the second set of parameters, wherein the second format includes the expected price of the pharmaceutical treatment being a price per pack for the pharmaceutical treatment;
cause display, at a second computing device, a second graphical user interface including the second set of parameters that adhere to the geographical limitation;
receive, over the network and via a second user input on the second graphical user interface, an offer to provide the pharmaceutical treatment comprising a third set of parameters, the third set of parameters being provided in a third format, and wherein the third set of parameters include an offer to provide price, the offer to provide price including an offered price per pack of the pharmaceutical;
convert the third set of parameters from the third format to the first format,
wherein converting the third set of parameters comprises converting the price per pack of the pharmaceutical treatment to the first format comprises converting the determined price per pack of the pharmaceutical treatment to a price per patient of the pharmaceutical treatment;
determine a probability of success of a negotiation between the purchaser and the provider, wherein the probability of success is based upon a percentage associated with a difference between the offer to purchase price and the offer to provide price; and
cause display, at the second computing device, a third graphical user interface including the third set of parameters and a recommendation to the purchaser or the provider based on the probability of success, the recommendation including a recommended adjustment for a subsequent round of negotiation, wherein the third set of parameters displayed to each of the plurality of providers is different based on a geographical limitation associated with each of the plurality of the providers.

13. The computerized system of claim 12, wherein the number of patients eligible for the pharmaceutical treatment may be one.

14. The computerized system of claim 12, wherein the first set of parameters comprises a maximum number of rounds of negotiations.

15. The computerized system of claim 12, wherein the pharmaceutical treatment comprises multiple therapies that can be used to treat a same disease or indication.

16. The computerized system of claim 12, wherein the indication to hide the one or more parameters is based on a country-specific rule.

17. The computerized system of claim 12, wherein the pharmaceutical treatment includes one or more products, the provider of the pharmaceutical treatment includes a plurality of providers, each of the plurality of providers associated with at least a portion of the one or more products.

18. The computerized system of claim 12, wherein the purchaser of the pharmaceutical treatment comprises a plurality of purchasers, each of the purchasers associated with at least a portion of the offer to provide price.

19. The computerized system of claim 12, wherein the purchaser of the pharmaceutical treatment comprises a plurality of purchasers and the second set of parameters displayed to each of the plurality of purchasers adheres to an anti-trust regulation.

20. The computerized system of claim 12, wherein the provider of the pharmaceutical treatment comprises a plurality of providers and the third set of parameters displayed to each of the plurality of providers adheres to an anti-trust regulation.

* * * * *